United States Patent [19]

Yen

[11] Patent Number: 4,855,113
[45] Date of Patent: Aug. 8, 1989

[54] APPARATUS FOR REMOVING SULFUR FROM ORGANIC POLYSULFIDES

[75] Inventor: Jeffrey H. Yen, Woolwich, N.J.

[73] Assignee: Pennwalt Corporation, Philadelphia, Pa.

[21] Appl. No.: 923,240

[22] Filed: Oct. 27, 1986

[51] Int. Cl.[4] .............................................. B01J 8/04
[52] U.S. Cl. .................... 422/259; 210/266; 210/273; 261/149; 422/191; 422/195; 422/257
[58] Field of Search ............... 422/193, 195, 171, 191, 422/257, 259; 261/149; 210/266, 273

[56] References Cited

U.S. PATENT DOCUMENTS

| | | | |
|---|---|---|---|
| 2,850,362 | 9/1958 | Scheibel | 422/259 |
| 3,433,600 | 3/1969 | Christensen et al. | 422/195 X |
| 3,488,159 | 1/1970 | Moon | 422/257 |
| 4,009,230 | 2/1977 | Smorenburg | 261/149 X |
| 4,028,171 | 6/1977 | Richter | 422/195 X |

OTHER PUBLICATIONS

Ziulkowki, "Liquid/Liquid Extraction in Chemical Industry," (translated from Polish to Russian), Leningrad, State Publishing House for Literature on Chemistry, 1963, pp. 344–347, Figures 4-23 thru 4-25.

Karpachova, et al., "Pulsating Extractors," Atomizdat Publishers, Moscow, 1964, pp. 71–72, 101, Table 3.1.

Alexandrov, "Rectification and Adsorption Apparatus (Procedures for Designing & Engineering)," Moscow-Leningrad, Khima Publishers, 1965, p. 247, Figure IX.1.

Ramm, "Gas Adsorption," Moscow, Khimia Publishers, 1966, pp. 380–383, Figures 116–119.

Perry's Chemical Engineers' Handbook, 5th Edition, McGraw-Hill Book Co., New York, N.Y., pp. 21-25,26.

Primary Examiner—Barry S. Richman
Assistant Examiner—Jill Johnston

[57] ABSTRACT

Sulfur-laden liquid organic phase dimethyl polysulfide (DMPS) is caused to rise from a sour gas well by reaction of the gaseous sulfur component within the well with a sulfur solvent, typically dimethyl disulfide (DMDS). The DMPS is contacted by an extraction or stripping liquid in a vertical column continuous multistage countercurrent flow extractor especially designed to promote high interfacial area contact between the liquids while flowing in opposing directions within the column.

9 Claims, 3 Drawing Sheets

APPARATUS FOR REMOVING SULFUR FROM ORGANIC POLYSULFIDES

CROSS-REFERENCE TO OTHER APPLICATIONS

Reference is made herein to application Ser. No. 878,163, filed June 25, 1986, of Yen et al., for "Process for Removing Sulfur from Organic Polysulfides", and assigned to the present assignee and now abandoned.

STATEMENT OF THE INVENTION

This invention relates to the removal of sulfur from dimethyl polysulfides (DMPS) formed by the reaction of $H_2S$, for example, contained within a sour gas well, with a sulfur solvent, typically dimethyl disulfide (DMDS), pumped into the well, and more particularly to an improved extractor for removing said sulfur efficiently and economically.

BACKGROUND AND SUMMARY OF THE INVENTION

Sulfur deposition in downhole tubular and wellhead equipment associated with sour gas wells is usually troublesome to sour gas producers. Elemental sulfur, $H_2S$, and polysulfides are the principal sources of these unwanted sulfur deposits.

Dialkyl disulfides, alkyl disulfides and polysulfides, and particularly dimethyl disulfide (DMDS), $CH_3SSCH_3$, are effective sulfur-dissolving agents or solvents for cleaning sulfur deposits. The relatively low flammability and vapor pressure of DMDS make it very attractive as a sulfur-dissolving solvent in sour gas wells. Further, DMDS can be efficiently regenerated through chemical wash. In the present application and aforementioned cross-referenced patent application, DMDS is regenerated in a multistage continuous countercurrent flow extractor.

Many processes in the prior art are known for the extraction of dissolved sulfur from solvents. For example, in U.S. Pat. Nos. 3,474,028, 3,489,677, 3,617,529, 3,748,827, 4,018,572, and 4,230,184, the use of alkali metal and ammonium hydrosulfides and sulfides to remove dissolved sulfur from mineral oils are disclosed. The publication of Dowling, Lesage, and Hyne for *Regeneration of Loaded Dimethyl Disulfide Based Sulfur Solvents*, Alberta Sulfur Research Limited Quarterly Bulletin, Vol. XXI, Nos. 3 & 4, pp. 30–52, October 1984–March 1985, discloses the regeneration of dimethyl disulfide by stripping sulfur from dimethyl polysulfide (DMPS) in a batch operation with alkali metal and ammonium hydrosulfides and sulfides, preferably sodium sulfide. None of the above prior art references discloses or suggests however the instant continuous multistage countercurrent flow extraction apparatus for removing sulfur from organic polysulfides.

The extractor apparatus of the present invention comprises a vertical multistage column extractor or reactor containing a distributor means at each end thereof, each of the stages comprising a packing section; a pair of redistributor plates with an agitator therebetween, each of the above recited components being spaced from each other, as well as from the packing section of an adjacent stage. A final packing section is provided adjacent that distributor means devoid of one adjacent thereto such that a packing section is disposed interiorly each distributor means.

The arrangement of components within the extractor and within each stage thereof insures efficient countercurrent flow of the two immiscible liquids, i.e., the stripping or extraction solution, typically aqueous $Na_2S$, and the sulfur-laden liquid organic phase (DMPS), such that high interfacial area contact is constantly maintained between the liquids.

DETAILED DESCRIPTION OF THE INVENTION

Although the invention is illustrated herein by dimethyl polysulfide (DMPS) as the sulfur bearing organic component requiring desulfurization, and aqueous sodium sulfide as the stripping solution, the invention is directed to improved apparatus which permits removal of sulfur from an organic polysulfide by contacting it with an aqueous solution of one or more sulfide salts and/or hydrosulfide salts of the formula $Y_2S$ or $ZSH$ wherein Y is selected from Group IA of the Periodic Table and a member of the group $NR_1R_2R_3R_4$ where $R_1$, $R_2$, $R_3$ and $R_4$ are independently selected from H, and alkyl of 1–20 carbons (such as methyl, butyl, cyclohexyl, and cetyl), aryl of 6–14 carbons (such as phenyl, naphthyl, and anthracenyl), and alkylaryl of 7–34 carbons (such as tolyl, dodecylphenyl, cetylphenyl, butynaphtyl, and butylanthracenyl). Z is selected from Y and Group IIA of the Periodic Table.

The reaction is carried out in a multi-stage, direct contact, countercurrent, continuous flow extractor, or reactor, preferably of stainless steel, such that said aqueous sulfide salt and/or hydrosulfide salt chemically reacts with said organic polysulfide to yield an aqueous polysulfide solution and an organic polysulfide of lower sulfur rank, i.e., a polysulfide wherein fewer sulfur atoms are present in each polysulfide molecule. The reaction is depicted by the following equation:

$$R'SS_pSR' + nY_2S \rightarrow R'SS_{(p-q)}SR' + nYSS_{q/n}Y$$

where $p > 0$ and $q \leq p$.

Temperature and pressure do not materially affect the performance of the process while operation at ambient conditions is preferred. Key parameters which must be considered are the choice and concentration of the aqueous stripping solution, period of contact between the DMPS and aqueous $Na_2S$, and the molar ratio of the aqueous $Na_2S$ to recoverable sulfur in the DMPS. Recoverable sulfur may be defined as that sulfur above rank two which is chemically incorporated into the DMPS. The definition of sulfur rank is well known to those skilled in the art. For example, the sulfur rank of DMDS is two. These parameters, such as temperature and pressure, for example, are constrained by the requirement that the difference in the densities of the organic and aqueous phases in each separation zone of the extractor apparatus be sufficient to allow efficient phase separation.

The following is a detailed discussion of the drawings in which like-numbered elements of the Figures are the same.

Figure 1:
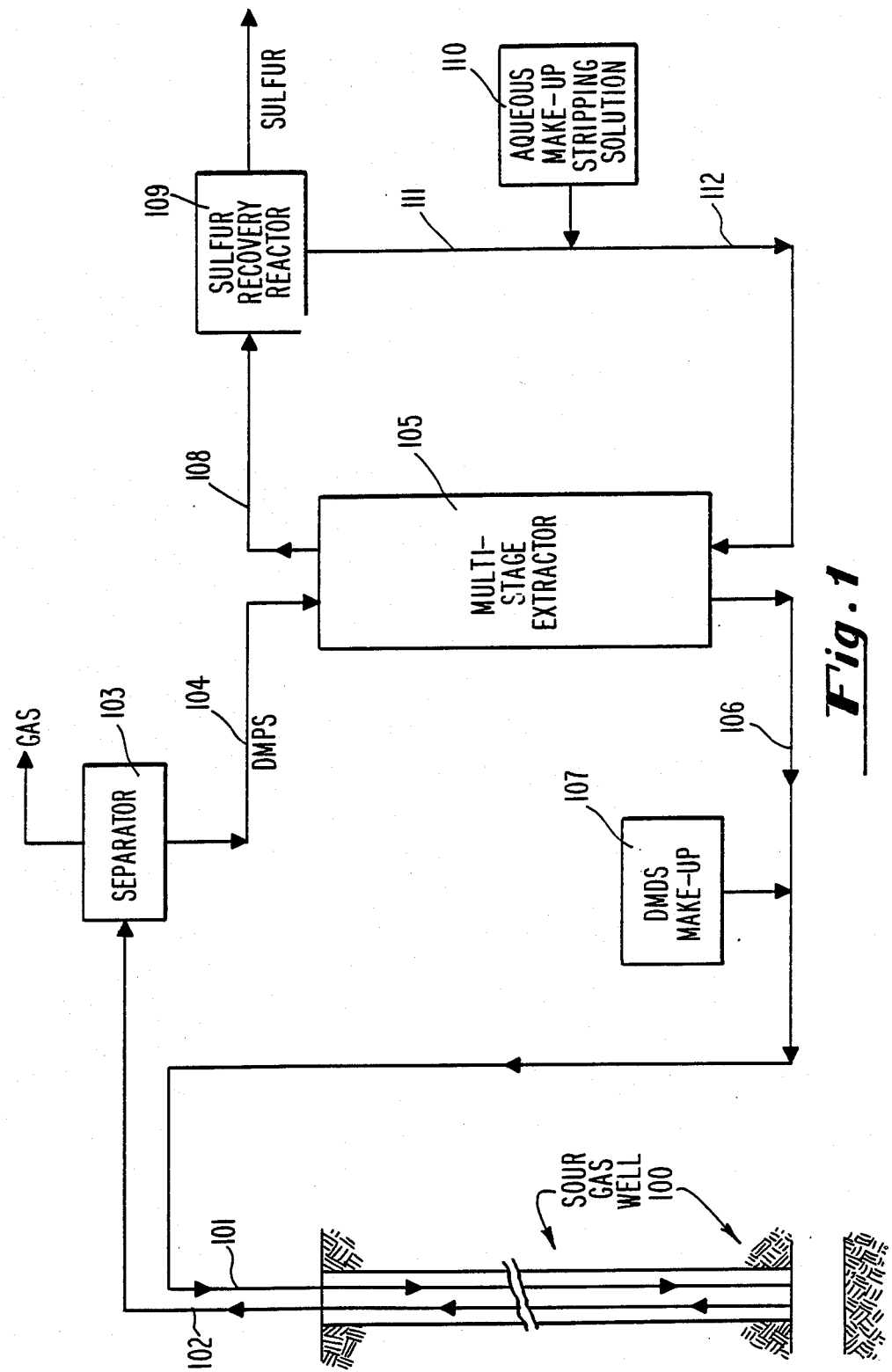
FIG. 1 is a flow diagram illustrating a process for removing sulfur from a dialkyl polysulfide formed within a sour gas well, the process employing the improved extractor apparatus of the present invention.

In FIG. 1, the density of DMPS is greater than the density of aqueous $Na_2S$.

In the processing of a sour gas well 100, sulfur often forms deposits which may plug the well to interrupt production. Such sulfur deposits may be removed by introducing a solvent for sulfur, such as dimethyl disulfide, downhole via line 101, optionally in the presence of a catalyst such as dimethyl formamide and sodium hydrosulfide, as is well known in the art. Dialkyl disulfides, alkyl sulfides, polysulfides, benzene, toluene, spindle oil, and the like, have also been used as solvents for controlling sulfur deposition. Riser pipe 102 delivers the sour gas and organic polysulfide, typically DMPS, formed by reaction of the sulfur in the well gases with the dimethyl disulfide, from the well 100 to separator 103 where the sour gas is separated from the organic polysulfide. The sour gas, typically, a mixture largely of methane, hydrogen sulfide, and carbon dioxide, is treated to separate its components and to convert the separated hydrogen sulfide to elemental sulfur via well known Claus technology. The dimethyl polysulfide is delivered via line 104 to multi-stage countercurrent flow stripping extractor 105 which separates elemental sulfur from the dimethyl disulfide, the latter being returned to the well 100 via lines 106 and 101 for reuse. Make-up dimethyl disulfide (and optionally catalyst) at 107 may be added to the regenerated dimethyl disulfide from extractor 105 to replace materials lost in processing.

The aqueous $Na_2S$ extracting or stripping solution is added to extractor or reactor 105 via line 112, and, as it passes countercurrently through extractor 105, reacts with the DMPS therein, the sulfur content of the stripping solution increasing. The now sulfur-laden aqueous stripping solution is discharged via line 108 to sulfur recovery reactor 109. Optionally, sulfur may be recovered in reactor 109 by adding a proton source, such, for example, as $H_2S$, $H_2SO_4$, $HNO_3$, and the like, and aqueous $Na_2S$ returned via lines 111 and 112 to extractor 105. Make-up stripping solution at 110 may be added to the recycled stripping solution from reactor 109 in line 112 to replace material lost in processing.

Separator 103 may comprise a lightweight cyclone, for exmple, relying heavily on centrifugal effects to generate efficient separation. The gaseous phase containing mostly $H_2S$ is discharged from the top of the cyclone while the DMPS and water settle in two separate phases at the bottom of the cyclone, each being pumped out from a different vane. Of course, other conventional separators may also be employed herein.

Figure 2:
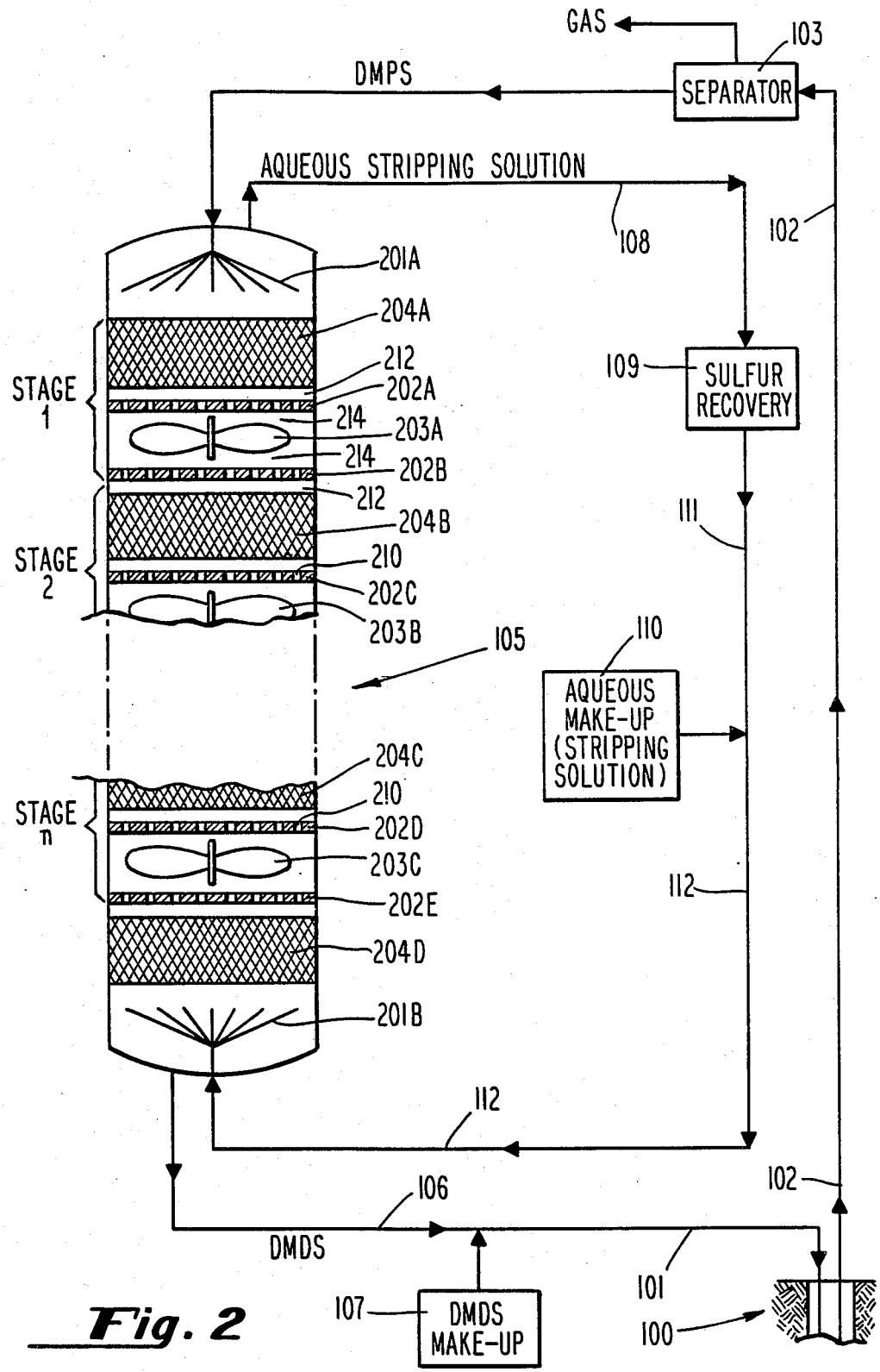
FIG. 2 diagrammatically illustrates a vertical section through the extractor of the present invention.

Multi-stage countercurrent flow extractor 105 (FIG. 2) is in the form of a vertical column having separate stages therein including distributors 201A and 201B; redistributor plates 202A, 202B, 202C, 202D and 202E; agitators 203A, 203B and 203C; and packing sections, elements or components 204A, 204B, 204C, and 204D.

Packing section 204A, redistributor plate 202A, agitator 203A and redistributor plate 202B comprise stage 1 of the extractor 105; while packing section 204C redistributor plate 202D, agitator 203C, and redistributor plate 202E comprise the extractor's final stage, or stage n.

Since DMPS, in this Figure, possesses a greater density than the aqueous $Na_2S$, the former is caused to flow into the extractor column at a top portion thereof via line 104 while the latter enters its bottom via line 112. The flow pattern, of course, would be reversed if the DMPS possessed a lower density. The DMPS is uniformly distributed or dispersed across a transverse cross-sectional area of the column by means of distributor 201A and similarly with the aqueous stripping solution at the lower end of the extractor column by distributor 201B. Distributors 201A and 201B are typically nozzles which provide a uniform flow pattern and may be purchased as an off-the-shelf item.

Assuming the extractor has been successfully operating for several minutes, the DMPS flowing downwardly intimately contacts the $Na_2S$ flowing in the opposite direction in packing section 204A, for example. The sulfur-laden DMPS possesses its highest sulfur content at the top of the column. Since the recoverable sulfur content in the aqueous stripping $Na_2S$ solution is negligible at the bottom of the extractor column, the driving potential i.e., the tendency of the chemical reaction of the above discussed equation to proceed from left to right for transferring the residual recoverable sulfur from the organic phase (DMPS) to the aqueous phase ($Na_2S$) is expected to be reasonably high.

The packing sections are typically Raschig Rings, Pall Rings, saddles, mesh screens, grid packing, and the like. Packing section thicknesses depend upon the velocity of the reactants through the extractor and the efficiency of the packing section material. The packing sections assist to provide a high interfacial contact area between the reactants and are considered essential to efficient extraction.

The circular redistribution plates 202, preferably stainless steel, are provided with spaced holes or orifices 210 therethrough.

The agitating means 203, powered electrically from a remote area by conventional means (not shown), is disposed between the redistributor plates of each stage and insure good mixing of the liquid reactants as well as maintaining continued direction of countercurrent travel of the respective liquids. The proper speed of rotation of the agitating means is regarded as critical if both objectives are to be attained. The speed of agitator rotation is generally determined empirically.

The redistributor plates tend to render the flow pattern of the liquids more uniform after they exit the packing sections, and serve to create a temporary barrier between the agitation zone and packing sections to aid in furthering optimum interfacial contact of the liquids. Spaces 212 are optionally provided between redistributor plates and packing sections; whereas spaces 214 are provided between each pair of redistributor plates of each stage and includes therein agitating means 203. Spaces 212 and 214 render the entire extraction process considerably more efficient.

Extractor columns of varying height can house stages of varying numbers depending upon process needs.

The aqueous stripping solution having a high foreign sulfur loading at the top portion of the extractor column coincides with the location or point where the DMPS has its highest recoverable sulfur content. At this point, a driving potential still exists between the aqueous stripping solution and the organic phase because of the relative concentration of sulfur in the two liquids. The sulfur-laden aqueous stripping solution is discharged from the top of the column via line 108 for disposal or optionally for further treatment.

Figure 3:
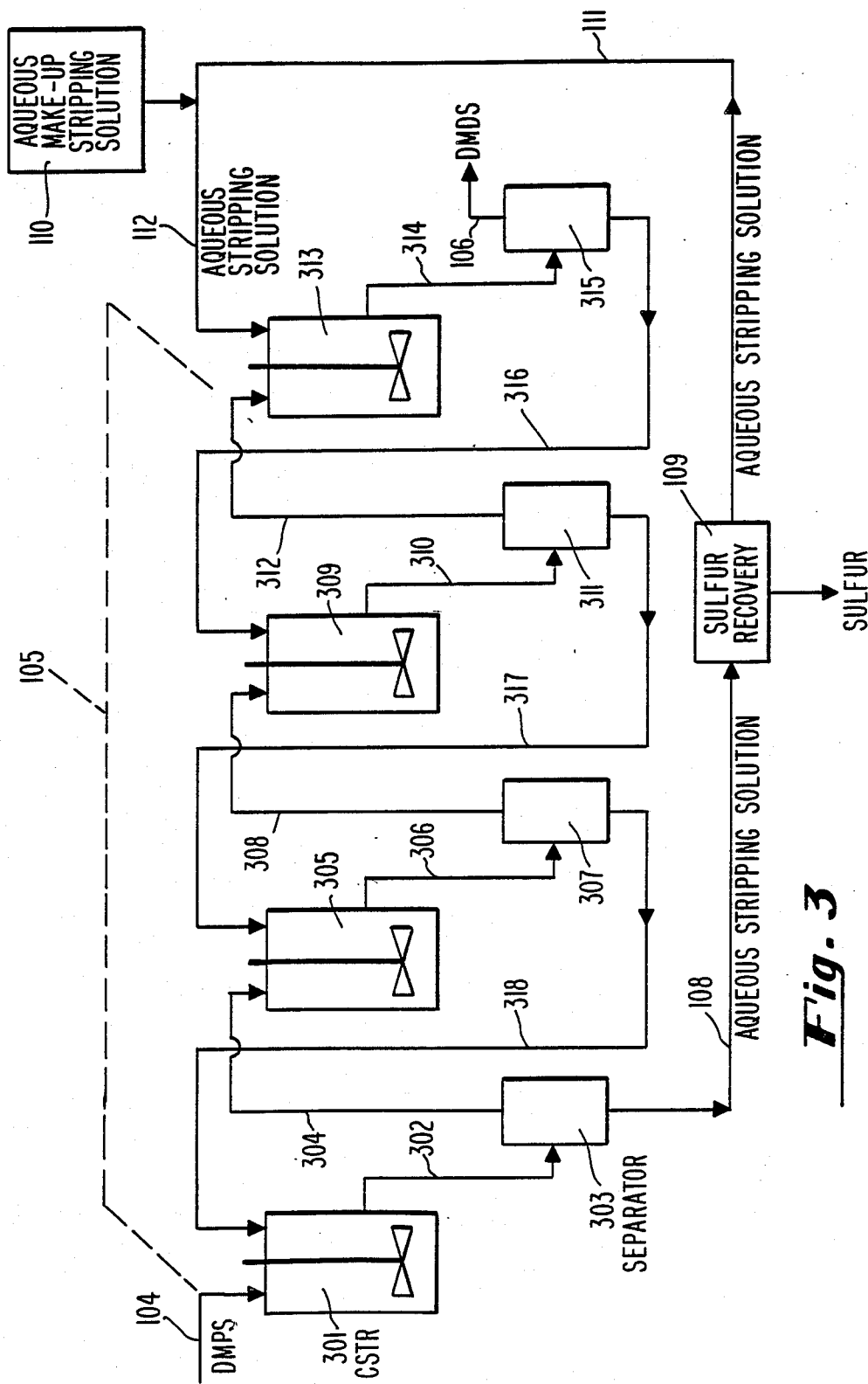
FIG. 3 is a flow diagram illustrating a process using a series of continuous stirring tank reactors (CSTR) and separators for removal of sulfur from DMPS.

In FIG. 3, each stage of the extractor 105 may comprise a separate reactor tank 301, 305, 309, 313 with a stirrer therein and a conduit 302, 306, 310, 314 respectively connecting each reactor tank to a separate phase separator tank 303, 307, 311, 315 wherein each of said stages is connected in series such that the organic phase from the first separator 303 is delivered directly into the second stage reactor tank 305 via line 304 and the organic phase from the second separator 307 is delivered into reactor tank 309 of the third stage via line 308, and the organic phase from the third separator 311 is delivered into reactor tank 313 of the fourth stage via line 312, until the organic phase from final separator 315 is the regenerated (i.e., lower rank sulfur content polysulfide) product via line 106; and the stripping solution from each separator 307, 311, 315 is returned via lines 318, 317, 316 respectively to the previous reactor stage 301, 305, 309 to comprise the stripping solution therein. In tank 313, fresh stripping solution is added thereto via lines 111 and 112 from aqueous make-up stripping solution 110 to flow countercurrently to and react with the organic polysulfide and thereafter to follow the flow pattern described above. Aqueous stripping solution containing foreign sulfur is removed from separator 303 via line 108 to be disposed of or optionally sent to sulfur recovery reactor 109 where sulfur is removed from the aqueous stripping solution; the aqueous stripping solution may then be returned to reactor tank 313 via lines 111 and 112. Obviously, if the density of the organic phase is heavier than that of the aqueous stripping solution, the abovementioned flow pattern will be reversed.

The preferred number of stages is a function of the degree of regeneration and recovery required; in most cases, two stages are sufficient.

Reactor tanks 301, 305, 309 and 313 may conveniently comprise conventional continuous stirring tank reactors (CSTR).

Among the sulfide salts and/or hydrosulfide salts suitable for use in the present invention, sodium sulfide in water is preferred, preferably at a concentration of between 10 weight percent and the saturation concentration of sodium sulfide at the operating temperature of the system.

The preferred reaction times (defined as the total liquid volume flow rate of the organic and aqueous phases divided by the sum of the available reaction volumes in the reactors) range from 5 to 120 minutes; generally the operation is complete in 30 minutes. At contact times shorter than 5 minutes regeneration is insufficient while contact times longer than 120 minutes do not result in significantly improved regeneration.

The molar ratio of the sulfide salt and/or hydrosulfide salt in the aqueous solution to the recoverable sulfur in the organic polysulfide (R value) may range from 0.10 to 0.70; the preferred range is 0.20 to 0.40. Using R values below 0.10 result in incomplete regeneration while using R values above 0.70 result in decreased recovery of the organic polysulfide.

The organic polysulfide need not necessarily originate from the downhole cleaning of a sour gas well. In the preparation of lower organic disulfides, the disulfides are frequently separated from their co-produced polysulfides by distillation. However, it is often not feasible to purify higher organic disulfides (e.g., butyl, hexyl, nonyl, etc.) by distillation because of decomposition and the apparatus of this invention can be employed to produce higher organic disulfides from their respective polysulfides.

EXAMPLE

Employing the system of FIG. 3, dimethyl polysulfide containing 25.9 weight % recoverable sulfur was reacted with a 17% aqueous solution of sodium sulfide in a continuous, countercurrent flow, direct contact two-stage system for a total of 5 minutes in the system. The molar ratio of the sodium sulfide to recoverable sulfur was 0.30. Values of 61% regeneration of the organic dimethyl disulfide and 92% recovery of the dimethyl disulfide were obtained.

For purposes of comparison, the same experiment was repeated except that a continuous single stage system was used in place of the multi-stage, countercurrent flow, direct contact system. The molar ratio of sodium sulfide to recoverable sulfur for this experiment was 0.40. Values of 61% regeneration of the organic dimethyl disulfide and 90% recovery of the dimethyl disulfide were obtained. Thus, the countercurrent, multi-stage technique of the present invention results in a savings of 25% of sodium sulfide over a single stage system.

Percent regeneration and percent recovery are redefined as follows:

$$\% \text{ Regeneration} = \frac{\text{wt \% } S_R \text{ (in)} - \text{wt \% } S_R \text{ (out)}}{\text{wt \% } S_R \text{ (in)}} \times 100$$

$$\% \text{ Recovery} = \frac{\text{wt Disulfide (in)}}{\text{wt Disulfide (out)}} \times 100$$

where $S_R$ is the sulfur that has been chemically incorporated into the organic polysulfide.

I claim:

1. A multistage continuous countercurrent flow extractor for removing sulfur from an organic polysulfide of high sulfur rank comprising a vertical column having a heavier liquid inlet at a first end and a lighter liquid inlet at a second end, said first end having an outlet for the lighter liquid after it traverses upwardly the length of said column and said second end having an outlet for the heavier liquid after it traverses downwardly the length of said column, the liquids being immiscible; distributor means interiorly adjacent each of said first and second ends and associated with said inlets for uniformly dispersing across a transverse cross-sectional area of the column each of the heavier and lighter liquids respectively; a plurality of successive similar stages disposed longitudinally within said column between each of said distributor means, each of said stages including components spaced from each other and from adjacent stages, each of said stages sequentially comprising, (a) a horizontally disposed packing section free of fluid-flow baffling means, (b) first redistributor means substantially horizontally coextensive with said packing section, (c) rotary agitating means, and (d) second redistributor means substantially horizontally coextensive with said packing section; and a final packing section below and adjacent to said second redistributor means of the final stage.

2. Apparatus of claim 1 wherein each of said packing sections assist in providing high interfacial area contact between the liquids traversing countercurrently in said column.

3. Apparatus of claim 2 wherein each of said agitating means rotates at a speed adapted to augment the higher interfacial area contact and to maintain the countercurrent directions of flow of the respective liquids.

4. Apparatus of claim 3 wherein said packing sections comprise Raschig Rings.

5. Apparatus of claim 3 wherein said packing sections comprise Pall Rings.

6. Apparatus of claim 3 wherein said packing sections comprise saddles.

7. Apparatus of claim 3 wherein said packing sections comprise mesh screens.

8. Apparatus of claim 3 wherein said packing sections comprise grid packing.

9. Apparatus of claim 3 wherein each of said redistributor means comprises circular plates having spaced orifices therethrough.

* * * * *